US011717442B2

(12) United States Patent
Steinlechner et al.

(10) Patent No.: US 11,717,442 B2
(45) Date of Patent: Aug. 8, 2023

(54) OPHTHALMOLOGICAL DEVICE AND METHOD FOR SURGICAL TREATMENT OF A CORNEA

(71) Applicant: Ziemer Ophthalmic Systems AG, Port (CH)

(72) Inventors: Michael Steinlechner, Zurich (CH); Christian Rathjen, Bremen (DE); Werner Bernau, Köniz (CH)

(73) Assignee: Ziemer Ophthalmic Systems AG, Port (CH)

( * ) Notice: Subject to any disclaimer, the term of this patent is extended or adjusted under 35 U.S.C. 154(b) by 72 days.

(21) Appl. No.: 17/130,616

(22) Filed: Dec. 22, 2020

(65) Prior Publication Data

US 2022/0192870 A1 Jun. 23, 2022

(51) Int. Cl.
*A61F 9/008* (2006.01)

(52) U.S. Cl.
CPC .... *A61F 9/008* (2013.01); *A61F 2009/00851* (2013.01); *A61F 2009/00872* (2013.01); *A61F 2009/00897* (2013.01)

(58) Field of Classification Search
CPC ............ A61F 9/008; A61F 2009/00851; A61F 2009/00872; A61F 2009/00897; A61F 9/00827
See application file for complete search history.

(56) References Cited

U.S. PATENT DOCUMENTS

| 7,621,637 | B2 | 11/2009 | Rathjen et al. |
| 10,575,989 | B2 | 3/2020 | Dishler et al. |

| 2011/0184394 | A1* | 7/2011 | Donitzky | A61F 9/00836 606/4 |
| 2013/0281992 | A1* | 10/2013 | Seiler | A61F 9/00827 606/5 |
| 2016/0089270 | A1 | 3/2016 | Fu | |
| 2017/0128261 | A1* | 5/2017 | Deisinger | A61F 9/00825 |
| 2019/0015250 | A1 | 1/2019 | Rathjen | |
| 2019/0015251 | A1 | 1/2019 | Rathjen | |
| 2019/0015253 | A1 | 1/2019 | Rathjen | |
| 2019/0175400 | A1* | 6/2019 | Loerner | A61F 9/00825 |
| 2020/0069470 | A1* | 3/2020 | Fu | A61F 9/0084 |

FOREIGN PATENT DOCUMENTS

| DE | 102016218564 A1 | 3/2017 | |
| WO | 2011088848 A1 | 7/2011 | |
| WO | WO-2014135218 A1 * | 9/2014 | ......... A61F 9/00836 |

* cited by examiner

*Primary Examiner* — Ahmed M Farah
*Assistant Examiner* — Sebastian X Lukjan
(74) *Attorney, Agent, or Firm* — Banner & Witcoff, Ltd.

(57) ABSTRACT

An ophthalmological device for surgical treatment of a cornea comprises a laser source, a focusing optical module, a scanner system, and an electronic circuit configured to control the scanner system to move the focus of the pulsed laser beam generated by the laser source to cut inside the cornea a lenticule and a venting channel which comprises an opening incision in a peripheral area of an exterior surface of the cornea, outside a perimeter of the lenticule from a top view perspective onto the cornea, and the venting channel connecting fluidically the posterior lenticule surface and/or the anterior lenticule surface to the opening incision, to enable venting of gas, produced by cutting the lenticule inside the cornea, through the opening incision to the exterior of the cornea.

19 Claims, 6 Drawing Sheets

OPHTHALMOLOGICAL DEVICE AND METHOD FOR SURGICAL TREATMENT OF A CORNEA

FIELD OF TECHNOLOGY

The present disclosure relates to an ophthalmological device and a method for surgical treatment of a cornea of an eye. In particular, the present disclosure relates to an ophthalmological device and a method for surgical treatment of a cornea of an eye using a pulsed laser beam, and to a computer program product with computer program code for controlling a processor of the ophthalmological device.

BACKGROUND

For the purposes of working on eye tissue by means of a laser beam, a work region is scanned by laser pulses by virtue of the pulsed laser beam being deflected in one or more scan directions by means of suitable scanner systems. In general, movable mirrors are used to deflect the light beams and/or the laser pulses, for example femtosecond laser pulses, said movable mirrors being pivotable about one or two scan axes, for example by way of galvano scanners, piezo scanners, polygon scanners, or resonance scanners.

U.S. Pat. No. 7,621,637 describes an apparatus for working on eye tissue, said apparatus having a base station with a laser source for producing laser pulses and a scanner, arranged in the base station, with movable deflection mirrors for deflecting the laser pulses in a scan direction. The deflected laser pulses are transferred via an optical relay system from the base station to an application head, the latter passing over a work region according to a scan pattern by means of a mechanically moved projection optical unit. According to U.S. Pat. No. 7,621,637, in the application head, the deflection in the scan direction, which is much faster in comparison with the mechanical movement, is overlaid onto the mechanical movement of the projection optical unit and consequently onto the scan pattern thereof. A fast scanner system in the base station facilitates a fine movement of the laser pulses (micro-scan), which is overlaid on the scan pattern of the movable projection optical unit that covers a large work region, for example the entire eye.

For refractive correction, pulsed laser radiation is used in corneal surgery to create a lenticule in the cornea. To achieve the refractive correction, the created lenticule is subsequently removed from the cornea through an extraction channel cut in the cornea.

US 2016/0089270 describes a system and a method for cutting lenticules in the eye tissue. According to US 2016/0089270, straight-lined fast scan lines are overlaid to this end on slower work lines that are traced out along meridians of the lenticule.

Using femtosecond laser pulses to generate cuts inside the cornea produces gas inside the cornea. As this gas produces cloudy areas in the cornea, it may impair the quality of subsequent neighbouring or overlapping cuts and thereby compromise significantly the quality of the cut surface and the intended refractive correction. To alleviate the negative impact of gas produced during the cutting process, WO 2011/088848 and DE102016218564 teach the cutting of venting pockets inside the cornea which receive and collect the unwanted gas. Nevertheless, when lenticules are cut inside the cornea for refractive correction, these venting pockets may still have a negative impact as the build-up of pressure by the gas inside the venting pockets may be detrimental to the precision of corneal cuts which is absolutely required for refractive correction.

SUMMARY

The present disclosure proposes an ophthalmological device and a method for surgical treatment of a cornea of an eye using a pulsed laser beam, which device and method do not have at least some of the disadvantages of the prior art. Particularly, the present disclosure proposes an ophthalmological device and a method for surgical treatment of a cornea of an eye using a pulsed laser beam, which device and method at least reduce the detrimental impact of gas produced when a lenticule is cut inside the cornea using the pulsed laser beam.

According to the present disclosure, one or more advantages over the prior art are achieved by the features of the independent claims. Moreover, further advantageous embodiments emerge from the dependent claims and the description. An ophthalmological device for surgical treatment of a cornea of an eye comprises: a laser source configured to generate a pulsed laser beam; a focusing optical module configured to make the pulsed laser beam converge onto a focus in the cornea; a scanner system configured to move the focus to target locations in the cornea; and an electronic circuit configured to control the scanner system to move the focus to cut inside the cornea a lenticule, the lenticule having a posterior lenticule surface and an anterior lenticule surface.

According to the present disclosure, the electronic circuit is further configured to control the scanner system to move the focus to cut in the cornea a venting channel, the venting channel comprising an opening incision in a peripheral area of an exterior surface of the cornea, outside a perimeter of the lenticule from a top view perspective onto the cornea, and the venting channel connecting fluidically at least one of the posterior lenticule surface or the anterior lenticule surface to the opening incision, to enable venting of a gas, produced by cutting the lenticule inside the cornea, through the opening incision to the exterior of the cornea.

In an embodiment, the ophthalmological device comprises a measurement system configured to determine positional reference data of the cornea, and the electronic circuit is configured to control the scanner system to move the focus to cut the venting channel, using the positional reference data. The positional reference data of the cornea is particularly useful for positioning the opening incision of the venting channel in the peripheral area of the exterior surface of the cornea, outside the perimeter of the lenticule from the top view perspective onto the cornea.

In an embodiment, the ophthalmological device further comprises a patient interface, the patient interface comprising an applanation body and one or more suction elements configured to fix the applanation body to the cornea for applanating the cornea in an applanation zone where the applanation body is in contact with the exterior surface of the cornea; and the electronic circuit is configured to control the scanner system to move the focus to cut in the cornea the venting channel with the opening incision located in a peripheral area of the exterior surface of the cornea outside the applanation zone.

In an embodiment, the patient interface comprises a fastening ring encompassing the applanation body, the one or more suction elements are arranged in the fastening ring and connected fluidically to a suction pump, and in the state where the patient interface is fixed to the cornea, the fastening ring and the applanation body form an external venting chamber with the peripheral area of the exterior surface of the cornea, outside the applanation zone; and the electronic circuit is configured to control the scanner system to move the focus to cut in the cornea the venting channel with the opening incision leading to the inside of the external venting chamber.

In an embodiment, the ophthalmological device further comprises a measurement system configured to determine positional reference data of the cornea in an applanated state of the cornea, and the electronic circuit is configured to control the scanner system to move the focus to cut the venting channel, using the positional reference data to position the opening incision of the venting channel in the peripheral area of the exterior surface of the cornea outside the applanation zone.

In an embodiment, the measurement system comprises a video capturing system and/or an optical coherence tomography system.

In an embodiment, the electronic circuit is configured to control the scanner system to move the focus to cut in the cornea an extraction channel, the extraction channel comprising an extraction incision in the exterior surface of the cornea, and the extraction channel connecting the lenticule to the extraction incision to enable extraction of the lenticule through the extraction incision to the exterior of the cornea; and to control the scanner system to move the focus to cut the venting channel partially coinciding with the extraction channel.

In an embodiment, the electronic circuit is configured to control the scanner system to move the focus along a work trajectory to cut the venting channel and at least one of the posterior lenticule surface or the anterior lenticule surface in a continuous movement of the focus along the work trajectory.

In an embodiment, the electronic circuit is configured to control the scanner system to move the focus to cut the venting channel from the opening incision to a perimeter of the lenticule, the perimeter being defined by an intersection of the posterior lenticule surface and the anterior lenticule surface.

In an embodiment, the electronic circuit is configured to control the scanner system to move the focus along a tangential trajectory for cutting the venting channel, whereby the tangential trajectory runs tangentially onto a perimeter of the lenticule.

In an embodiment, the electronic circuit is configured to control the scanner system to move the focus along a spiral shaped trajectory to cut at least one of the posterior lenticule surface or the anterior lenticule surface, and to move the focus along a straight trajectory that leads onto the spiral shaped trajectory to cut the venting channel along the straight trajectory.

In an embodiment, the electronic circuit is configured to control the scanner system to move the focus along a radial trajectory directed towards a central axis of the lenticule to cut the venting channel along the radial trajectory.

In an embodiment, the electronic circuit is configured to control the scanner system to move the focus to cut the venting channel with a channel width which increases from the lenticule to the opening incision.

In an embodiment, the electronic circuit is configured to control the scanner system to move the focus to cut in the cornea a first venting channel, the first venting channel comprising a first opening incision in the exterior surface of the cornea, and the first venting channel connecting the posterior lenticule surface to the first opening incision, to enable venting of a gas produced by cutting the posterior lenticule surface through the first opening incision to the exterior of the cornea, and to cut in the cornea a second venting channel, the second venting channel comprising a second opening incision in the exterior surface of the cornea, and the second venting channel connecting the anterior lenticule surface to the second opening incision, to enable venting of a gas produced by cutting the anterior lenticule surface through the second opening incision to the exterior of the cornea.

In addition to the ophthalmological device for surgical treatment of a cornea of an eye, the present disclosure further relates to a computer program product, particularly, a computer program product comprising a non-transitory computer-readable medium having stored thereon computer program code for controlling a processor of an ophthalmological device which comprises a laser source configured to generate a pulsed laser beam, a focusing optical module configured to make the pulsed laser beam converge onto a focus in the cornea, and a scanner system configured to move the focus to target locations in the cornea. The computer program code is configured to control the processor such that the processor directs the scanner system to move the focus to cut inside the cornea a lenticule, the lenticule having a posterior lenticule surface and an anterior lenticule surface, and to move the focus to cut in the cornea a venting channel, the venting channel comprising an opening incision in a peripheral area of an exterior surface of the cornea, outside a perimeter of the lenticule from a top view perspective onto the cornea, and the venting channel connecting fluidically at least one of the posterior lenticule surface or the anterior lenticule surface to the opening incision, to enable venting of a gas produced by cutting the lenticule inside the cornea through the opening incision to the exterior of the cornea.

In addition to the ophthalmological device and the computer program product, the present disclosure further relates to a method of surgical treatment of a cornea of an eye, the method comprising: generating, by a laser source, a pulsed laser beam; making, by a focusing optical module, the pulsed laser beam converge onto a focus in the cornea; moving, by a scanner system, the focus to target locations in the cornea; and controlling, by an electronic circuit, the scanner system to move the focus to cut inside the cornea a lenticule, the lenticule having a posterior lenticule surface and an anterior lenticule surface, and to move the focus to cut in the cornea a venting channel, the venting channel comprising an opening incision in a peripheral area of an exterior surface of the cornea, outside a perimeter of the lenticule from a top view perspective onto the cornea, and the venting channel connecting fluidically at least one of the posterior lenticule surface or the anterior lenticule surface to the opening incision, to enable venting of a gas produced by cutting the lenticule inside the cornea through the opening incision to the exterior of the cornea.

BRIEF DESCRIPTION OF THE DRAWINGS

The present disclosure will be explained in more detail, by way of example, with reference to the drawings in which.

DETAILED DESCRIPTION OF THE EMBODIMENTS

Figure 1:
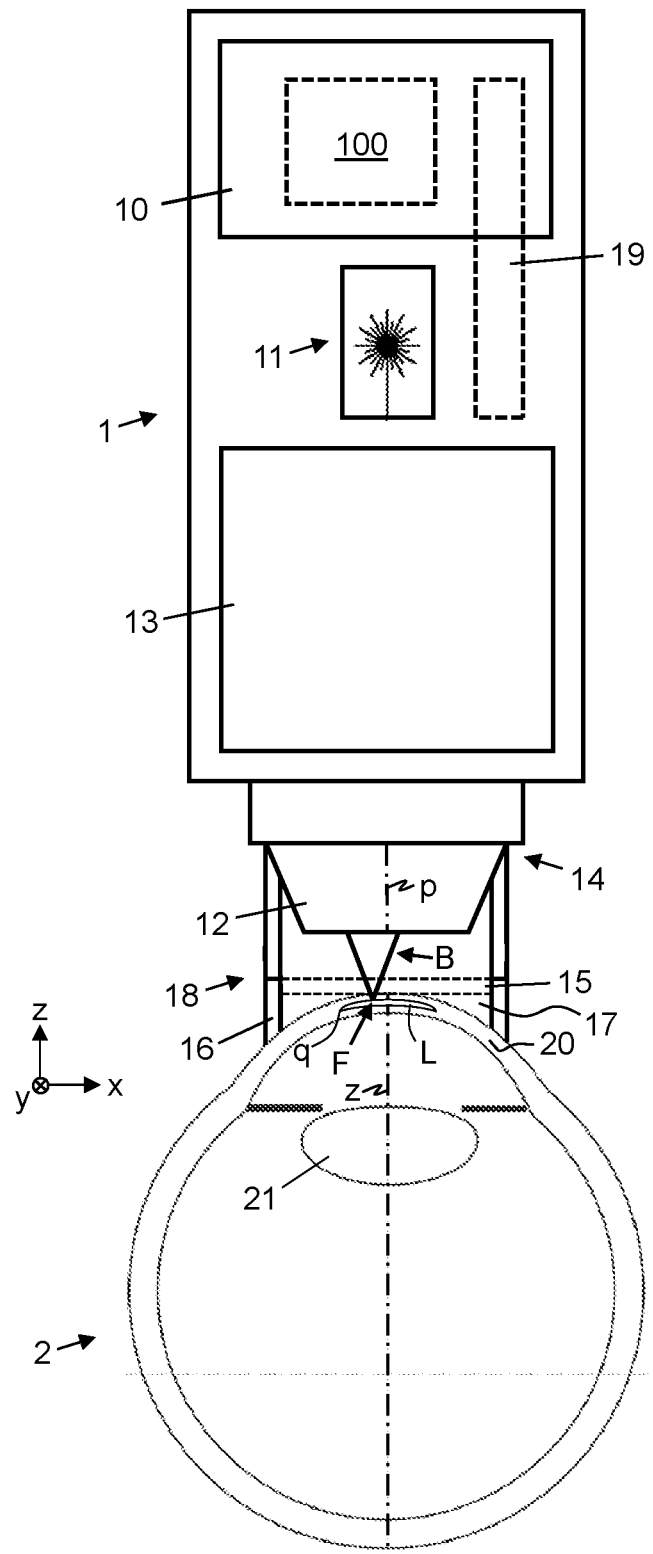
FIG. 1 shows a block diagram that schematically illustrates an ophthalmological device for surgical treatment of a cornea with a pulsed laser beam, said device comprising a focusing optical module for focusing the pulsed laser beam in the cornea, and a scanner system for moving the focus to target locations in the cornea.

In FIG. 1, reference numeral 1 relates to an ophthalmological device for surgical treatment of a cornea 20 of an eye 2 with a pulsed laser beam B.

As illustrated schematically in FIG. 1, the ophthalmological device 1 comprises a laser source 11 for generating the pulsed laser beam B, a focusing optical module 12 for focusing the pulsed laser beam B in the cornea 20 onto a focus F, and a scanner system 13 for moving the focus F to target locations in the cornea 20.

In particular, the laser source 11 comprises a femtosecond laser for producing femtosecond laser pulses, which have pulse widths of typically 10 fs to 1000 fs (1 fs=$10^{-15}$ s). The laser source 11 is arranged in a separate housing or in a housing shared with the focusing optical module 12.

The focusing optical module 12 is configured to focus the pulsed laser beam B or the laser pulses, respectively, in the cornea 20 onto a focus F, i.e. for making the pulsed laser beam B converge to a focal point or spot in the cornea 20. The focusing optical module 12 comprises one or more optical lenses. In an embodiment, the focusing optical module 12 comprises a focus adjustment device for setting the focal depth of the focus F, for example one or more movable lenses, in the focusing optical module 12 or upstream of the focusing optical module 12, or a drive for moving the entire focusing optical module 12 along the projection axis p (z-axis). By way of example, the focusing optical module 12 is installed in an application head 14, which can be placed onto the eye 2.

As illustrated schematically in FIG. 1, the ophthalmological device 1 comprises a patient interface 18 for attaching the application head 14 or the focusing optical module 12, respectively, onto the eye 2. Depending on the embodiment, the patient interface 18 is connected to the application head 14 in a fixed or removable manner.

The patient interface 18 comprises an applanation body 15 and one or more suction elements configured to fix the applanation body 15 and thus the patient interface 18 to the cornea 20. For example, the one or more suction elements are arranged in a fastening ring 16, e.g. a vacuum-controlled suction ring, whereby the one or more suction elements are connected fluidically to a suction pump. The applanation body 15, also referred to as contact body, is at least partly light-transparent.

Figure 2:
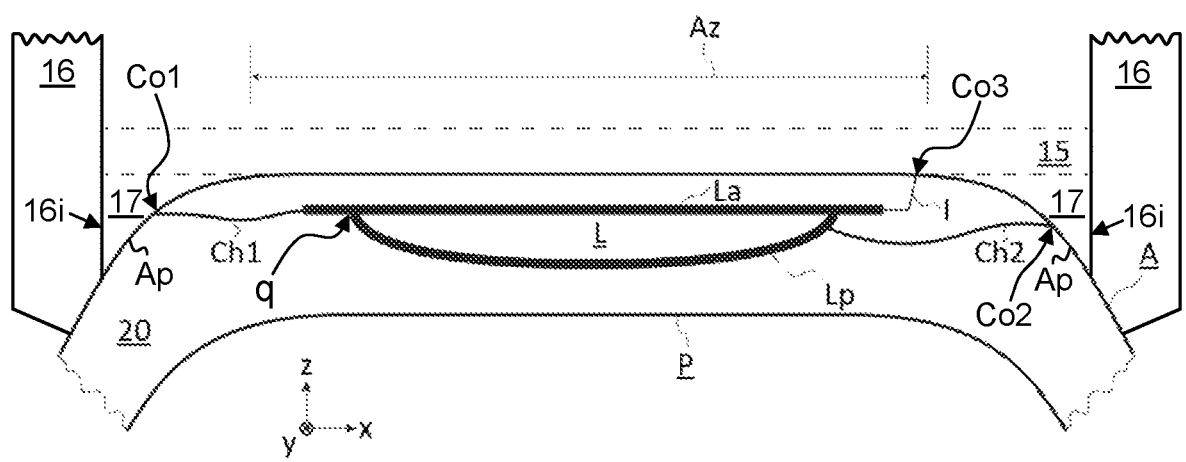
FIG. 2 shows a schematic cross-sectional view of a cornea with a lenticule cut in the cornea, and a first venting channel and a second venting channel cut in the cornea to enable venting of gas, produced by cutting the lenticule inside the cornea, to the exterior of the cornea.

As illustrated in FIG. 2, in the state where the patient interface 18 or the applanation body 15, respectively, is fixed to the cornea 20, specifically to the exterior (anterior) surface A of the cornea 20, applanated is an applanation zone Az of the cornea 20, where the applanation body 15 is in contact with the exterior (anterior) surface A of the cornea 20.

As is further illustrated in FIG. 2 and also indicated in FIG. 1, in the state where the patient interface 18 or the applanation body 15, respectively, is fixed to the cornea 20, the fastening ring 16 and the applanation body 15 form an external venting chamber 17 with the peripheral area Ap of the exterior (anterior) surface A of the cornea 20 outside the applanation zone Az. The venting chamber 17 is defined by an interior wall 16i of the fastening ring 16, the surface of the applanation body 15 contacting the cornea 20, and the peripheral area Ap of the exterior (anterior) surface A of the cornea 20 outside the applanation zone Az.

The scanner system 13 is configured to move the focus F to target locations in the cornea 20 by guiding and directing the pulsed laser beam B and thus the focus F to target locations in the cornea 20. The scanner system 13 comprises one or more scanner modules configured to guide and direct the pulsed laser beam B and thus the focus F in a x/y-work-plane which is normal to a z-axis, whereby the z-axis is aligned with or essentially parallel to the projection axis p of the focusing optical module 12, as illustrated schematically in FIG. 1. Depending on the embodiment, the one or more scanner modules comprise one or more actuators configured to move the focusing optical module 12 such that the focus F is moved along a work line in the x/y-work-plane, and/or one or more deflection mirrors, each movable about one or two axes, configured to deflect the pulsed laser beam B and/or the laser pulses such that the focus F is moved along the work line in the x/y-work-plane. The scanner system 13 further comprises a z-modulator configured to move the focus F along the z-axis which is aligned with or essentially parallel to the projection axis p of the focusing optical module 12. For example, the z-modulator comprises a divergence modulator configured to dynamically change the divergence of the pulsed laser beam B. Various further and more specific embodiments of the scanner system 13 are described by the applicant in patent applications US 2019/0015250, US 2019/0015251, and US 2019/0015253 which are hereby incorporated by reference in their entireties.

The ophthalmological device 1 further comprises an electronic circuit 10 for controlling the laser source 11 and the scanner system 13. The electronic circuit 10 implements a programmable control device and comprises e.g. one or more processors 100 with program and data memory and programmed software modules for controlling the processors 100, and/or other programmable circuits or logic units such as ASICs (application specific integrated circuits).

In an embodiment, the ophthalmological device 1 further comprises a measurement system 19 configured to determine positional reference data of the cornea 20. Depending on the embodiment, the measurement system 19 comprises a video capturing system, an optical coherence tomography (OCT) system, and/or a structured light illumination system. Accordingly, the measurement data or positional reference data determined by the measurement system 19 includes video data, including top view data (comprising two-dimensional images), and/or OCT data of the cornea 20 (comprising three-dimensional tomography data). The measurement system 19 is configured to determine the positional reference data of the cornea 20 also in an applanated state of the cornea 20. The measurement system 19 is connected to and/or integrated with the electronic circuit 10 which is further configured to control the scanner system 13, using the positional reference data from the measurement system 19. For example, the measurement system 19 and/or the electronic circuit 10 are configured to determine as further positional reference data the peripheral area Ap of the exterior (anterior) surface A of the cornea 20 outside the applanation zone Az, using the measurement data or the positional reference data captured by the measurement system 19.

The electronic circuit 10 is configured to control the scanner system 13 to move the focus F to cut inside the cornea 20 a lenticule L which has a posterior lenticule surface Lp and an anterior lenticule surface La, as illustrated in FIG. 2. For example, the electronic circuit 10 is configured to control the scanner system 13 to move the focus F to cut the lenticule L inside the cornea 20 as described by the applicant in patent applications US 2019/0015250, US 2019/0015251, and US 2019/0015253 which are hereby incorporated by reference in their entireties.

The electronic circuit 10 is further configured to control the scanner system 13 to move the focus F to cut in the cornea 20 one or more venting channels Ch, Ch1, Ch2, as illustrated in FIGS. 2-6. These venting channels Ch, Ch1, Ch2, in FIGS. 2-6 provide a fluidic connection from the posterior lenticule surface Lp and/or the anterior lenticule surface La to respective opening incisions Co, Co1, Co2 in the exterior (anterior) surface A of the cornea 20. As illustrated in FIGS. 2-6, the venting channels Ch, Ch1, Ch2 comprise an opening incision Co, Co1, Co2 in a peripheral area of the exterior (anterior) surface A of the cornea 20, outside a perimeter of the lenticule L when viewed from a top view perspective (along the z-axis or the projection axis p, respectively) onto the cornea 20. The venting channels Ch, Ch1, Ch2 connect fluidically the lenticule L, specifically the posterior lenticule surface Lp and/or the anterior lenticule surface La, through the respective opening incisions Co, Co1, Co2 in the exterior (anterior) surface A of the cornea 20 to the exterior of the cornea 20.

The fluidic venting channels Ch, Ch1, Ch2 enable venting of gas, produced by (laser) cutting the lenticule L inside the cornea 20, through the respective opening incisions Co, Co1, Co2 to the exterior of the cornea 20. The venting channels Ch, Ch1, Ch2 have a channel width d, d1, d2 defined by the width of the cut surface forming the venting channels Ch, Ch1, Ch2. As can be seen in FIGS. 3-6, the channel width d, d1, d2 is defined by the extension of the cut surfaces forming the venting channels Ch, Ch1, Ch2 in a horizontal x/y-working plane. The channel width d, d1, d2 of the venting channels Ch, Ch1, Ch2 is far smaller than the length of the venting channels Ch, Ch1, Ch2, extending from the respective opening incisions Co, Co1, Co2 to the lenticule L. The relatively smaller channel widths d, d1, d2 or diameter of the cross-sectional profile of the venting channels Ch, Ch1, Ch2 is in the range of 0.1 mm to 0.8 mm, preferably in the range of 0.1 mm to 0.6 mm, whereas the length of the venting channels Ch, Ch1, Ch2 is in the range of 1 mm to 6 mm. In an embodiment, the venting channels Ch, Ch1, Ch2 are cut with a cross-shaped cross sectional profile of the venting channels Ch, Ch1, Ch2.

The electronic circuit 10 is further configured to control the scanner system 13 to move the focus F to cut in the cornea 20 the one or more venting channels Ch, Ch1, Ch2 from the outside to the inside of the cornea 20, i.e. commencing from the respective opening incision Co, Co1, Co2 in the exterior (anterior) surface A of the cornea 20 through the cornea tissue to the lenticule L inside the cornea 20.

In an embodiment, the electronic circuit 10 is further configured to control the laser source 11 to set and use a comparatively higher energy level for cutting the opening incisions Co, Co1, Co2 in the exterior (anterior) surface A of the cornea 20, and to reduce the energy level for cutting the venting channels Ch, Ch1, Ch2 beyond the opening incision Co, Co1, Co2.

It should be pointed out that cutting the one or more venting channels Ch, Ch1, Ch2 from the outside to the inside of the cornea produces gas which at least partially remains in the venting channels Ch, Ch1, Ch2 and keeps the venting channels Ch, Ch1, Ch2 open.

As is shown in FIGS. 2-6, the opening incisions Co, Co1, Co2 of the venting channels Ch, Ch1, Ch2 are arranged in a peripheral area Ap of the exterior (anterior) surface A of the cornea 20, outside the applanation zone Az. Thus, the fluidic venting channels Ch, Ch1, Ch2 enable the venting of the gas, produced by (laser) cutting the lenticule L inside the cornea 20, through the respective opening incisions Co, Co1, Co2 to the exterior of the cornea 20 outside the applanation zone Az. More specifically, the opening incisions Co, Co1, Co2 of the venting channels Ch, Ch1, Ch2 are arranged in a peripheral area Ap of the exterior (anterior) surface A of the cornea 20 bordering onto the venting chamber 17. Thus, the fluidic venting channels Ch, Ch1, Ch2 enable the venting of the gas, produced by (laser) cutting the lenticule L inside the cornea 20, through the respective opening incisions Co, Co1, Co2 into the venting chamber 17.

In an embodiment, the one or more suction elements of the fastening ring 16 apply—interruptedly or non-interruptedly—a partial vacuum to the venting chamber 17 and thereby further facilitate the venting of the gas, build-up by cutting the lenticule L in the cornea 20, through the fluidic venting channels Ch, Ch1, Ch2 and their respective opening incisions Co, Co1, Co2 to the exterior of the cornea 20, outside the applanation zone Az, into the venting chamber 17.

In an embodiment, the electronic circuit 10 is configured to use the positional reference data from the measurement system 19 to control the scanner system 13 to move the focus F to cut in the cornea 20 the one or more venting channels Ch, Ch1, Ch2. For example, the electronic circuit 10 is configured to determine from the measurement data or the positional reference data, respectively, the peripheral area Ap of the exterior (anterior) surface A of the cornea 20, outside the applanation zone Az. More specifically, the electronic circuit 10 is configured to determine from the measurement data or the positional reference data, respectively, the peripheral area Ap of the exterior (anterior) surface A of the cornea 20, outside the applanation zone Az and bordering onto the venting chamber 17. Moreover, the electronic circuit 10 is configured to determine the location of the opening incisions Co, Co1, Co2 inside the peripheral area Ap of the exterior (anterior) surface A of the cornea 20. In an embodiment, the electronic circuit 10 is configured to receive operator input, e.g. via a data entry element and/or a touchscreen, for selecting, moving, and/or positioning the location of the opening incisions Co, Co1, Co2 within the peripheral area Ap of the exterior (anterior) surface A of the cornea 20, Furthermore, the electronic circuit 10 is configured to control the scanner system 13 to move the focus F to cut in the cornea 20 one or more "mechanical" extraction channels I, as illustrated in FIGS. 2-6. As illustrated, an extraction channel I comprises an extraction incision Co3 in the exterior (anterior) surface A of the cornea 20. The extraction channel I connects the lenticule L to the extraction incision Co3 and enables mechanical extraction of the lenticule L from the cornea 20 through the extraction incision Co3 to the exterior of the cornea 20. Thus, compared to the channel widths d, d1, d2 of the fluidic venting channels Ch, Ch1, Ch2, the mechanical extraction channel I has much greater channel width d3, e.g. in the range of 2 mm to 5 mm. On the other hand, compared to the channel lengths of the fluidic venting channels Ch, Ch1, Ch2, the mechanical extraction channel I has much shorter channel length, e.g. in the range of 0.1 mm to 1.5 mm.

In an embodiment, the electronic circuit 10 is configured to control the scanner system 13 to move the focus F to cut in the cornea 20 the one or more venting channels Ch, Ch1, Ch2 partially coinciding with the extraction channel I.

Figure 3:
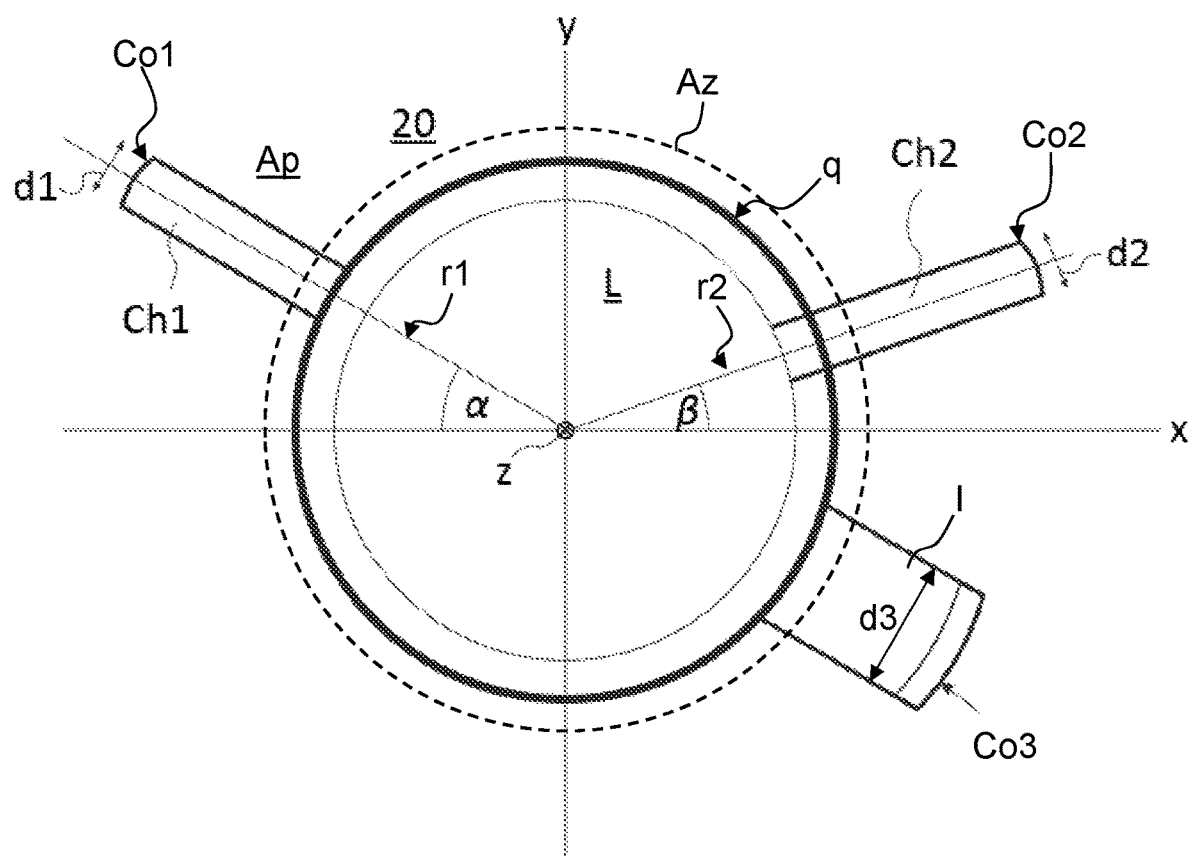
FIGS. 3-5 show schematic top views of a cornea with a lenticule cut in the cornea, and one or more venting channels cut in the cornea to enable venting of gas, produced by cutting the lenticule inside the cornea, to the exterior of the cornea.

In the following paragraphs, different embodiments and/or configurations of the venting channels Ch, Ch1, Ch2 are described with reference to FIGS. 2-6, whereby FIG. 2 shows a cross-sectional view of the venting channels Ch1, Ch2, and FIGS. 3-6 show top views of the venting channels Ch, Ch1, Ch2. For the sake of clarity, it is pointed out here that the electronic circuit 10 is configured to control the scanner system 13 to move the focus F to cut the venting channels Ch, Ch1, Ch2 in the cornea 20 to produce one or more of these embodiments and/or configurations and combinations thereof, for example, as selected or selectable by an operator. Furthermore, it is pointed out that FIGS. 2 and 3 show two venting channels Ch1, Ch2 with their respective opening incisions Co1, Co2, but that in different scenarios both or only one of these two venting channels Ch1, Ch2 may actually be cut, e.g. as selected by the operator.

Although it is only clearly visible in FIG. 2, it should be pointed out that all venting channels Ch, Ch1, Ch2 comprise an opening incision Co, Co1, Co2 within the peripheral area Ap of the exterior (anterior) surface A of the cornea 20, outside the applanation zone Az and bordering onto the venting chamber 17, such as to enable venting of gas through the venting channels Ch, Ch1, Ch2 and the respective opening incision Co, Co1, Co2 into the venting chamber 17.

FIGS. 3-6 show scenarios where the electronic circuit 10 is configured to control the scanner system 13 to move the focus F to cut the venting channel Ch, Ch1, Ch2 in the cornea 20 from the respective opening incision Co, Co1, Co2 to a perimeter q of the lenticule L. As illustrated in FIG. 2, the perimeter q of the lenticule L is defined by the intersection of the posterior lenticule surface Lp and the anterior lenticule surface La.

FIG. 3 shows a scenario where the electronic circuit 10 is configured to control the scanner system 13 to move the focus F along a radial trajectory r1, r2 directed towards a central axis z of the lenticule L to cut one or more of the venting channels Ch1, Ch2 along the respective radial trajectory r1, r2. As illustrated in FIG. 3, the radial trajectories r1, r2 are orientated at different angles α, β, e.g. with respect to a reference axis in the x/y-work plane, e.g. with respect to the x-axis, e.g. selected or set by the operator. As further illustrated in FIG. 3, the venting channels Ch1, Ch2 have different channel widths d1, d2, e.g. selected or set by the operator.

Figure 4:
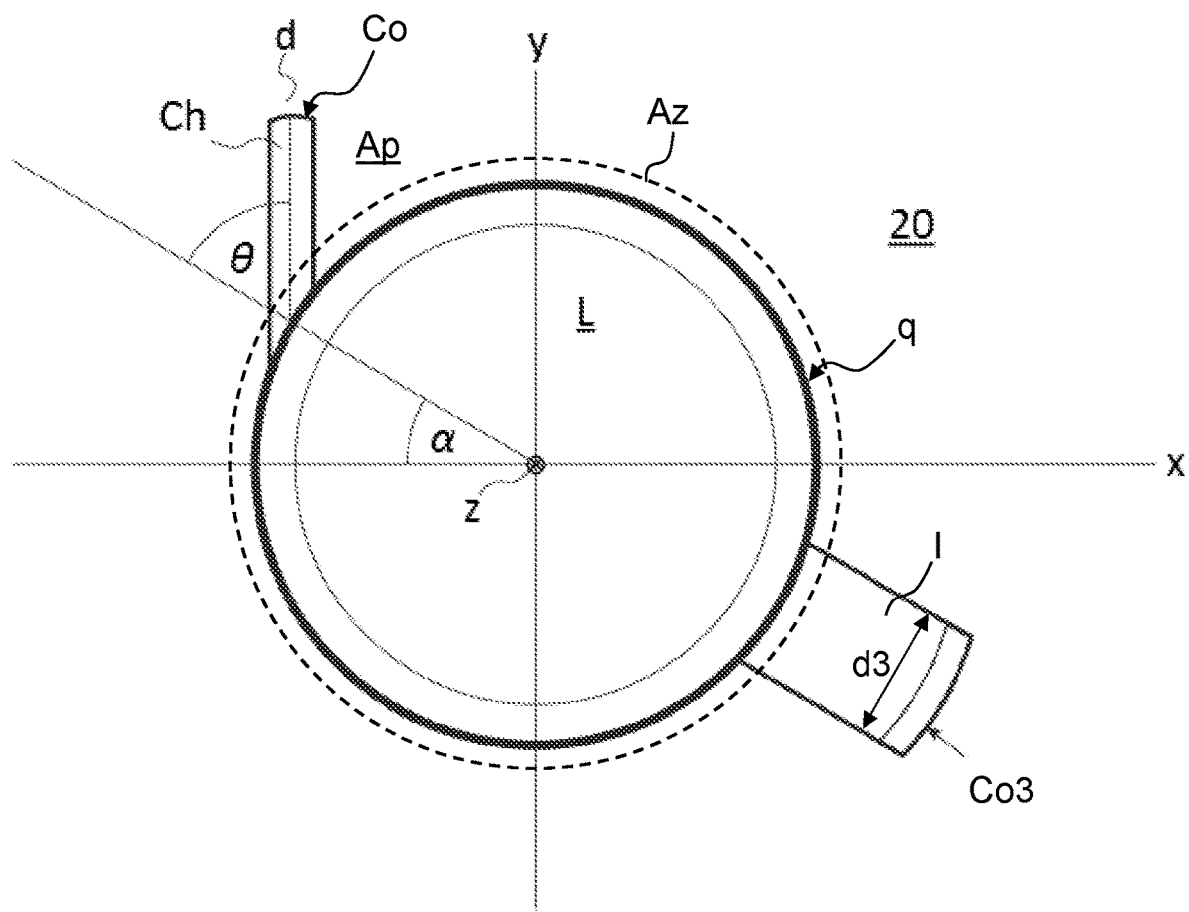
Figure 5:
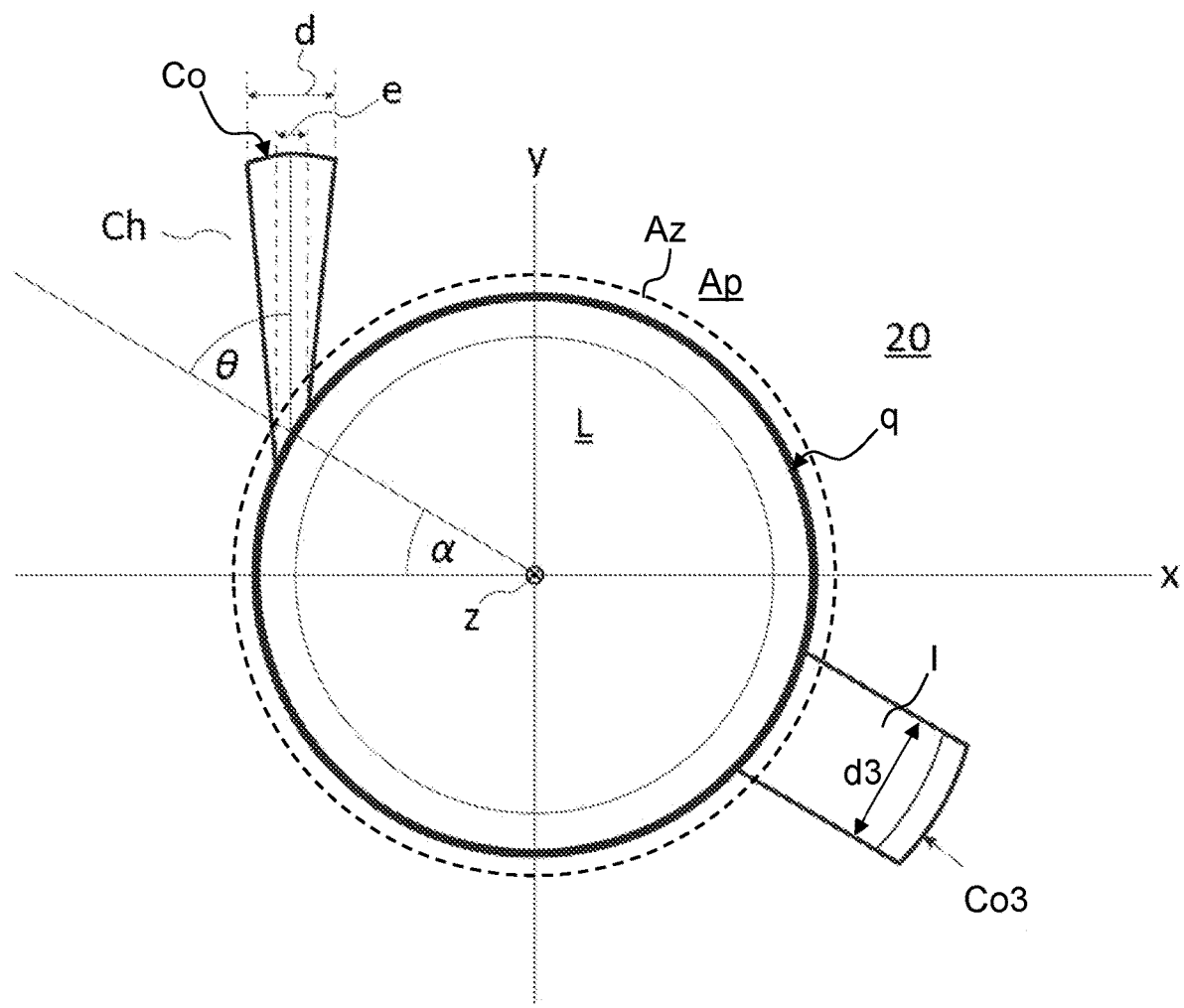

Contrary to FIG. 4, where the venting channel Ch has a constant channel width d from the opening incision Co to the perimeter q of the lenticule L, FIG. 5 shows a scenario where the electronic circuit 10 is configured to control the scanner system 13 to move the focus F to cut the venting channel Ch with a channel width which increases from the lenticule L to the opening incision Co, starting with a comparatively smaller channel width e onto the perimeter q of the Lenticule L and increasing to a comparatively wider channel width d at the opening incision Co.

Figure 6:
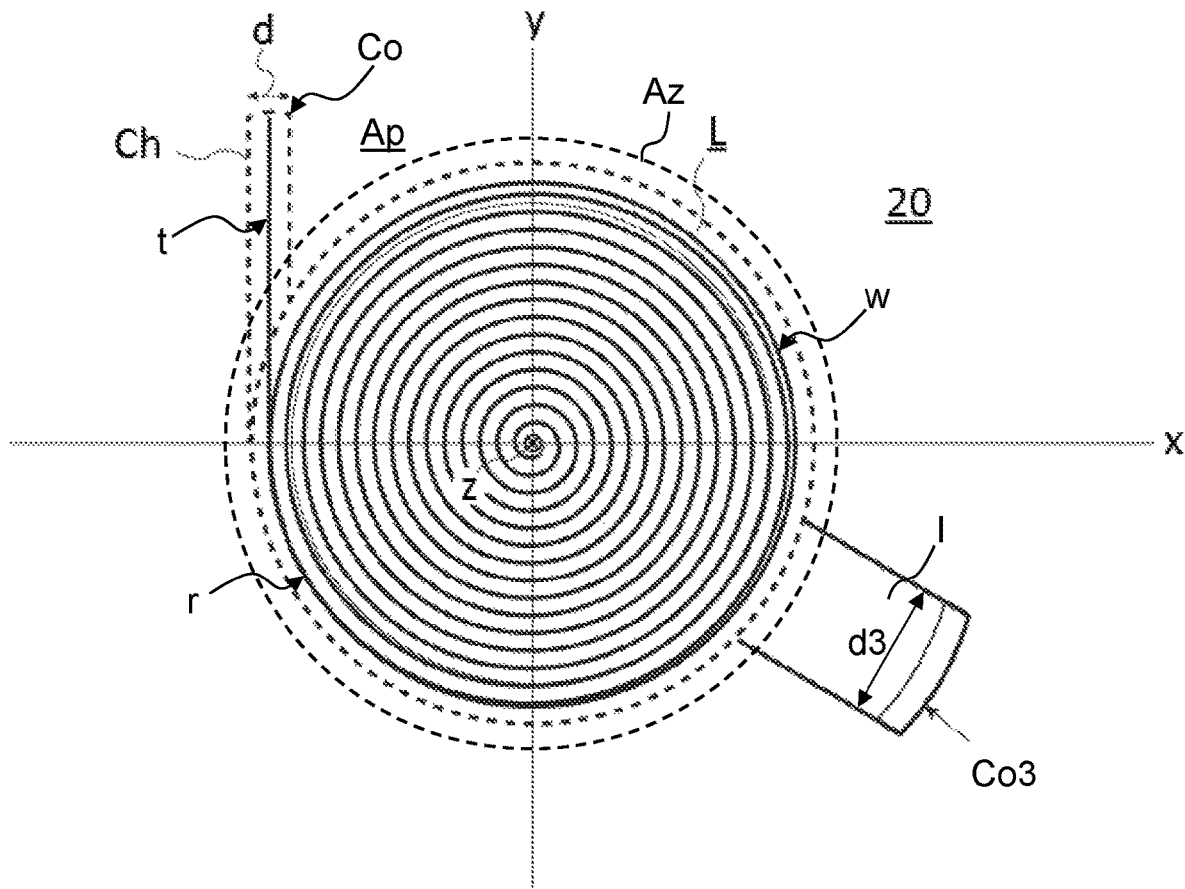
FIG. 6 shows a schematic top view of a cornea with a lenticule and a venting channel, cut in the cornea in a continuous movement of the focus along the same work trajectory, to enable venting of gas, produced by cutting the lenticule inside the cornea, to the exterior of the cornea.

FIG. 6 shows a scenario where the electronic circuit 10 is configured to control the scanner system 13 to move the focus F along a tangential trajectory t to cut the venting channel Ch, whereby the tangential trajectory t runs tangentially onto a perimeter q of the lenticule L.

FIG. 6 shows a scenario where the electronic circuit 10 is configured to control the scanner system 13 to move the focus F along a work trajectory w, e.g. a spiral shaped work trajectory w, to cut the venting channel Ch and the posterior lenticule surface Lp and/or the anterior lenticule surface La of the lenticule L in a continuous movement of the focus F along the work trajectory w.

FIG. 6 shows a scenario where the electronic circuit 10 is configured to control the scanner system 13 to move the focus F along a spiral shaped work trajectory w, to cut the posterior lenticule surface Lp and/or the anterior lenticule surface La of the lenticule L, and to move the focus F along a straight trajectory t that leads onto the spiral shaped work trajectory w to cut the venting channel Ch along the straight trajectory t.

In conclusion, it should be pointed out that the one or more venting channels Ch, Ch1, Ch2 need not be cut in a straight line but, as one skilled in the art will understand, could be cut along a curved trajectory (not illustrated).

What is claimed is:

1. An ophthalmological device for surgical treatment of a cornea of an eye, the ophthalmological device comprising:
   a patient interface, the patient interface comprising a contact body and at least one suction element configured to fix the contact body to the cornea for contacting the cornea in a contact zone, where the contact body is in contact with an exterior surface of the cornea;
   a laser source configured to generate a pulsed laser beam;
   a focusing optical module configured to make the pulsed laser beam converge onto a focus in the cornea;
   a scanner system configured to move the focus to target locations in the cornea; and
   an electronic circuit configured to control the scanner system to move the focus to cut inside the cornea a lenticule, the lenticule having a posterior lenticule surface and an anterior lenticule surface,
   wherein the electronic circuit is further configured to control the scanner system to move the focus to cut in the cornea a venting channel, the venting channel comprising an opening incision in a peripheral area of an exterior surface of the cornea, outside a perimeter of the lenticule from a top view perspective onto the cornea and outside the contact zone, and the venting channel connecting fluidically at least one of the posterior lenticule surface or the anterior lenticule surface to the opening incision, to enable venting of gas produced by cutting the lenticule inside the cornea through the opening incision to the exterior of the cornea outside the contact zone,
   wherein the electronic circuit is further configured to control the scanner system to move the focus along a work trajectory to cut the venting channel and at least one of the posterior lenticule surface or the anterior lenticule surface in a continuous movement of the focus along the work trajectory leading from the venting channel onto the posterior lenticule surface or the anterior lenticule surface.

2. The ophthalmological device of claim 1, wherein the ophthalmological device comprises a measurement system configured to determine positional reference data of the cornea, and the electronic circuit is configured to control the scanner system to move the focus to cut the venting channel, using the positional reference data.

3. The ophthalmological device of claim 1, wherein the contact body comprises an applanation body and the contact zone comprises an applanation zone.

4. The ophthalmological device of claim 3, wherein the patient interface comprises a fastening ring encompassing the applanation body, the at least one suction element is arranged in the fastening ring and connected fluidically to a suction pump, and in a state where the patient interface is fixed to the cornea the fastening ring and the applanation body form an external venting chamber with the peripheral area of the exterior surface of the cornea outside the applanation zone; and the electronic circuit is configured to control the scanner system to move the focus to cut in the cornea the venting channel with the opening incision opening inside the external venting chamber.

5. The ophthalmological device of claim 3, wherein the ophthalmological device comprises a measurement system configured to determine positional reference data of the cornea in an applanated state of the cornea, and the electronic circuit is configured to control the scanner system to move the focus to cut the venting channel, using the positional reference data to position the opening incision of the venting channel in the peripheral area of the exterior surface of the cornea outside the applanation zone.

6. The ophthalmological device of claim 5, wherein the measurement system comprises at least one of a video capturing system or an optical coherence tomography system.

7. The ophthalmological device of claim 1, wherein the electronic circuit is configured to control the scanner system to move the focus to cut in the cornea an extraction channel, the extraction channel comprising an extraction incision in the exterior surface of the cornea, and the extraction channel connecting the lenticule to the extraction incision to enable extraction of the lenticule through the extraction incision to the exterior of the cornea; and to control the scanner system to move the focus to cut the venting channel partially coinciding with the extraction channel.

8. The ophthalmological device of claim 1, wherein the electronic circuit is configured to control the scanner system to move the focus to cut the venting channel from the opening incision to a perimeter of the lenticule, the perimeter being defined by an intersection of the posterior lenticule surface and the anterior lenticule surface.

9. The ophthalmological device of claim 1, wherein the electronic circuit is configured to control the scanner system to move the focus along a tangential trajectory for cutting the venting channel, whereby the tangential trajectory runs tangentially onto a perimeter of the lenticule.

10. The ophthalmological device of claim 1, wherein the electronic circuit is configured to control the scanner system to move the focus along a spiral shaped trajectory to cut at least one of the posterior lenticule surface or the anterior lenticule surface, and to move the focus along a straight trajectory that leads onto the spiral shaped trajectory to cut the venting channel along the straight trajectory.

11. The ophthalmological device of claim 1, wherein the electronic circuit is configured to control the scanner system to move the focus along a radial trajectory directed towards a central axis of the lenticule to cut the venting channel along the radial trajectory.

12. The ophthalmological device of claim 1, wherein the electronic circuit is configured to control the scanner system to move the focus to cut the venting channel with a channel width which increases from the lenticule to the opening incision.

13. The ophthalmological device of claim 1, wherein the electronic circuit is configured to control the scanner system to move the focus to cut in the cornea a first venting channel, the first venting channel comprising a first opening incision in the exterior surface of the cornea, and the first venting channel connecting the posterior lenticule surface to the first opening incision, to enable venting of a gas produced by cutting the posterior lenticule surface through the first opening incision to the exterior of the cornea, and to cut in the cornea a second venting channel, the second venting channel comprising a second opening incision in the exterior surface of the cornea, and the second venting channel connecting the anterior lenticule surface to the second opening incision, to enable venting of a gas produced by cutting the anterior lenticule surface through the second opening incision to the exterior of the cornea.

14. A computer program product comprising a non-transitory computer-readable medium having stored thereon computer program code for controlling a processor of an ophthalmological device which comprises a patient interface, the patient interface comprising a contact body and at least one suction element configured to fix the contact body to the cornea for contacting the cornea in a contact zone, where the contact body is in contact with an exterior surface of the cornea, a laser source configured to generate a pulsed laser beam, a focusing optical module configured to make the pulsed laser beam converge onto a focus in a cornea, and a scanner system configured to move the focus to target locations in the cornea, whereby the computer program code is configured to control the processor such that the processor:
  directs the scanner system to move the focus to cut inside the cornea a lenticule, the lenticule having a posterior lenticule surface and an anterior lenticule surface, and to move the focus to cut in the cornea a venting channel, the venting channel comprising an opening incision in a peripheral area of an exterior surface of the cornea, outside a perimeter of the lenticule from a top view perspective onto the cornea and outside the contact zone, and the venting channel connecting fluidically at least one of the posterior lenticule surface or the anterior lenticule surface to the opening incision, to enable venting of a gas produced by cutting the lenticule inside the cornea through the opening incision to the exterior of the cornea outside the contact zone, and
  directs the scanner system to move the focus along a work trajectory to cut the venting channel and at least one of the posterior lenticule surface or the anterior lenticule surface in a continuous movement of the focus along the work trajectory leading from the venting channel onto the posterior lenticule surface or the anterior lenticule surface.

15. A method of surgical treatment of a cornea of an eye, the method comprising:
  fixing, by at least one suction element, a contact body to the cornea for contacting the cornea in a contact zone, where the contact body is in contact with an exterior surface of the cornea;
  generating, by a laser source, a pulsed laser beam;
  making, by a focusing optical module, the pulsed laser beam converge onto a focus in the cornea;
  moving, by a scanner system, the focus to target locations in the cornea; and
  controlling, by an electronic circuit, the scanner system to move the focus to cut inside the cornea a lenticule, the lenticule having a posterior lenticule surface and an anterior lenticule surface, and to move the focus to cut in the cornea a venting channel, the venting channel comprising an opening incision in a peripheral area of an exterior surface of the cornea, outside a perimeter of the lenticule from a top view perspective onto the cornea and outside the contact zone, and the venting channel connecting fluidically at least one of the posterior lenticule surface or the anterior lenticule surface to the opening incision, to enable venting of a gas produced by cutting the lenticule inside the cornea through the opening incision to the exterior of the cornea outside the contact zone, and to move the focus along a work trajectory to cut the venting channel and at least one of the posterior lenticule surface or the anterior lenticule surface in a continuous movement of the focus along the work trajectory leading from the venting channel onto the posterior lenticule surface or the anterior lenticule surface.

16. The method of claim 15, further comprising determining positional reference data of the cornea and controlling the scanner system to move the focus to cut the venting channel, using the positional reference data.

17. The method of claim 15, further comprising fixing an applanation body to the cornea for applanating the cornea in an applanation zone where the applanation body is in contact with the exterior surface of the cornea and controlling the scanner system to move the focus to cut in the cornea the venting channel with the opening incision located in a peripheral area of the exterior surface of the cornea outside the applanation zone.

18. The method of claim 15, further comprising:
controlling the scanner system to move the focus to cut in the cornea an extraction channel, the extraction channel comprising an extraction incision in the exterior surface of the cornea, and the extraction channel connecting the lenticule to the extraction incision to enable extraction of the lenticule through the extraction incision to the exterior of the cornea; and
controlling the scanner system to move the focus to cut the venting channel partially coinciding with the extraction channel.

19. The method of claim 15, further comprising controlling the scanner system to move the focus to cut the venting channel with a channel width which increases from the lenticule to the opening incision.

\* \* \* \* \*